(12) United States Patent
Barraclough et al.

(10) Patent No.: US 8,329,875 B2
(45) Date of Patent: Dec. 11, 2012

(54) ANTIBODIES TO AN EPITOPE OF AGR2, ASSAYS AND HYBRIDOMAS

(75) Inventors: Roger Barraclough, Liverpool (GB); Dong Liu Barraclough, Liverpool (GB); Philip Rudland, Liverpool (GB)

(73) Assignee: The University Of Liverpool (GB)

( * ) Notice: Subject to any disclaimer, the term of this patent is extended or adjusted under 35 U.S.C. 154(b) by 511 days.

(21) Appl. No.: 12/310,599

(22) PCT Filed: Aug. 28, 2007

(86) PCT No.: PCT/GB2007/003235
§ 371 (c)(1), (2), (4) Date: Feb. 26, 2009

(87) PCT Pub. No.: WO2008/025964
PCT Pub. Date: Mar. 6, 2008

(65) Prior Publication Data
US 2011/0052586 A1 Mar. 3, 2011

(30) Foreign Application Priority Data

Aug. 26, 2006 (GB) .................................. 0616929.6

(51) Int. Cl.
| | |
|---|---|
| *C12Q 1/00* | (2006.01) |
| *G01N 33/00* | (2006.01) |
| *G01N 33/53* | (2006.01) |
| *G01N 33/567* | (2006.01) |
| *G01N 33/574* | (2006.01) |
| *G01N 33/48* | (2006.01) |
| *G01N 21/00* | (2006.01) |
| *G01N 21/75* | (2006.01) |
| *C12N 5/02* | (2006.01) |
| *C12N 5/06* | (2006.01) |
| *C12N 5/16* | (2006.01) |
| *C12N 5/00* | (2006.01) |

(52) U.S. Cl. ......... 530/388.8; 435/4; 435/7.1; 435/7.21; 435/7.23; 435/7.92; 435/325; 435/326; 435/330; 435/331; 435/344; 436/63; 436/64; 436/164; 436/166; 436/172; 436/174; 436/501; 530/300; 530/350; 530/385; 530/386; 530/387.1; 530/387.7; 530/387.9; 530/388.15

(58) Field of Classification Search ........................ None
See application file for complete search history.

(56) References Cited

U.S. PATENT DOCUMENTS

| 6,822,072 B1 * | 11/2004 | Edwards et al. ............... 530/300 |
| 2002/0111303 A1 * | 8/2002 | Boyd et al. ....................... 514/12 |
| 2004/0141974 A1 | 7/2004 | Boyd et al. |
| 2004/0146907 A1 * | 7/2004 | Smith ............................... 435/6 |

FOREIGN PATENT DOCUMENTS

| WO | WO 03/075014 | * | 9/2003 |
| WO | 2004/031239 A2 | | 4/2004 |
| WO | 2005/040813 A1 | | 5/2005 |

OTHER PUBLICATIONS

Fletcher, et al.; hAG-2 and hAG-3, Human Homologues of Genes Involved in Differentiation, are Associated with Oestrogen Receptor-Positive Breast Tumours and Interact with Metastasis Gene C4.4a and Dystroglycan, Br. J. Canc., 2003, 88, 579-585.
Innes et al.; Significance of the Metastasis-Inducing Protein AGR2 for Outcome in Hormonally Treated Breast Cancer Patients, Br. J. Canc., Apr. 10, 2006 94:7, 1057-1065.
Dong et al.; Human Homologue of Cement Gland Protein, A Novel Metastasis Inducer Associated with Breast Carcinomas, Canc. Res., May 1, 2005, 65:9, 3796-3805.
International Search Report and Written Opinion, PCT/GB2007/003235, dated Apr. 8, 2008.

* cited by examiner

*Primary Examiner* — Alana Harris Dent
(74) *Attorney, Agent, or Firm* — Lerner, David, Littenberg, Krumholz & Mentlik, LLP

(57) ABSTRACT

Provided is a monoclonal antibody, or an antigen binding fragment thereof, which binds specifically to an epitope within the sequence KPGAKKDTKDSRPKL (Sequence ID No. 2) of AGR2. Such monoclonal antibodies are of prognostic and diagnostic utility in the investigation of cancer, particularly metastatic cancer. The antibodies described may also be used in prognosis or diagnosis of inflammatory diseases. Also provided are kits and solid supports comprising such antibodies, as well as the therapeutic use of antibodies of the invention.

18 Claims, 5 Drawing Sheets

ANTIBODIES TO AN EPITOPE OF AGR2, ASSAYS AND HYBRIDOMAS

Figure 1:

The present application is a national phase entry under 35 U.S.C. § 371 of International Application No. PCT/GB2007/003235, filed Aug. 28, 2007, published in English, which claims the benefit of Great Britain Patent Application No. 0616929.6, filed Aug. 26, 2006. The disclosures of said applications are incorporated by reference herein.

The present invention relates to monoclonal antibodies and to antigen-binding fragments of such monoclonal antibodies. The invention also relates to hybridomas capable of producing such antibodies. Further aspects of the invention also relate to uses of the monoclonal antibodies disclosed in diagnostic and prognostic assays for metastatic disease.

The anterior gradient 2 protein (AGR2) is the human homologue of the *Xenopus* cement gland-specific gene (XAG-2). The amino acid sequence of AGR2 is shown in Sequence ID No. 1. Increased expression of AGR2 has been shown to correlate with estrogen receptor (ER) positivity in breast carcinoma specimens. Induced expression of AGR2 appears to bring about a metastatic phenotype in otherwise benign non-metastatic cells.

Cancer is the second most common cause of death in the Western world, and is the leading cause of death among those under 85 years of age. One in four of the population will die of cancer, and these deaths generally occur as a result of untreatable metastatic disease. Dissemination of metastases throughout the body increases the number of tissues damaged by cancer, while simultaneously rendering treatment of the cancer increasingly difficult. The number of metastases that may develop from a single primary tumour will generally be too large to treat, and the number of different sites requiring treatment too numerous and varied.

The ability of metastatic cancers to "return" or "appear", even after excision or resolution of a primary tumour and systemic treatment, contributes greatly to the difficulties experienced in treating cancer, and also to the distress suffered by cancer patients uncertain as to whether or not a treatment has been effective to render them free from cancer.

It will be appreciated, in the light of the grave influence of cancer on the population as a whole, that there is a well-recognised need for methods that may be used to diagnose metastatic cancer (metastatic disease). Many existing methods lack sensitivity and/or reliability, and so the results of these methods cannot be viewed as conclusive. A reduced sensitivity of diagnostic assays may lead to incorrect diagnoses being made based on the incorrect assay results.

There is also a need for assays that may be used prognostically to assess a patient's likelihood of developing metastatic cancer. The limitations of sensitivity and reliability of existing assays for metastatic disease also mean that certain patients with an increased risk of developing metastatic disease are not necessarily identified using existing assays. The inability to identify such patients may mean that opportunities for therapeutic intervention prior to the appearance of symptoms of metastatic disease are lost.

There is also a need for prognostic assays that are able to indicate whether or not a patient will respond favourably to treatment for metastatic cancer. In general treatments for metastatic cancer comprise relatively "harsh" regimes. Such treatment regimes, and the ill-effects that they may cause, are generally justified in the case of patients who may not be expected to respond to less rigorous treatment. However it will generally be preferred to avoid subjecting patients who are likely to respond favourably to more "gentle" treatment to unnecessary harsh regimes.

It is an aim of certain embodiments of the invention to overcome or alleviate problems associated with the prior art. For example, it is an aim of certain embodiments of the present invention to provide diagnostic assays for metastatic disease that are more sensitive than those provided by the prior art. It is an aim of certain embodiments of the present invention to provide diagnostic assays for metastatic disease that are more reliable than those provided by the prior art. It is an aim of certain embodiments of the invention to provide prognostic assays for metastatic disease that are more sensitive than those provided by the prior art. It is an aim of certain embodiments of the invention to provide prognostic assays for metastatic disease that are more reliable than those provided by the prior art. It is an aim of certain embodiments of the invention to provide agents that may be used in diagnostic and/or prognostic assays for metastatic disease having greater sensitivity and/or reliability than those provided by the prior art.

In a first aspect, the invention provides monoclonal antibody, or an antigen binding fragment thereof, which binds specifically to an epitope within the sequence KPGAKKDTKDSRPKL (Sequence ID No. 2) of AGR2.

Sequence ID No. 2 corresponds to the 26$^{th}$ to 40$^{th}$ amino acid residues of human AGR2. The inventors have found that a monoclonal antibody, or antigen binding fragment thereof, having the specificity defined above provides notable advantages in use compared to prior art antibodies against AGR2. In particular, antibodies of the invention may be used in prognostic or diagnostic assays for cancer, and particularly metastatic disease, that have greater sensitivity than do similar assays provided by the prior art. Although expression of AGR2 is strongly associated with mammary cancers the expression of this marker is also present in a wide range of cancers including oesophageal squamous cell carcinoma, pancreatic carcinoma and prostate carcinomas. Accordingly, the inventors believe that the antibodies and methods of the invention may be used in connection with cancer, and metastatic disease, associated with any form of primary cancer. "Antibodies of the invention", as referred to in the present disclosure, may be any monoclonal antibody having specificity for an epitope within the sequence KPGAKKDTKDSRPKL (Sequence ID No. 2) of AGR2. The antibody produced by the hybridoma PZ7A10F10 represents a particularly preferred example of an antibody of the invention. PZ7A10F10 was deposited under the Budapest Treaty at the European Collection of Cell Cultures (ECACC), at Porton Down, Salisbury, UK, on 22 Aug. 2006, and was given the Accession Number 06082201. The monoclonal antibody produced by this hybridoma may, for the purposes of the present disclosure, be referred to as "anti-AGR2/PZ7A10F10". Anti-AGR2/PZ7A10F10, or antigen-binding fragments thereof, represents a preferred antibody, or preferred antigen-binding fragments, for use in all aspects and embodiments of the invention. AGR2/PZ7A10F10 is an IgG, κ light chain antibody.

As used in the present disclosure the term antibody of the invention should, unless the context requires otherwise, also be taken to encompass antigen-binding fragments of antibodies of the invention, as well as antigen-binding derivatives of such antibodies or antibody fragments.

Any suitable antigen-binding fragment(s) of the antibodies of the invention may be prepared according to techniques known to those skilled in the art. The smallest functional antigen-binding fragments of antibodies of the invention may comprise the variable regions of either the heavy (VH) or light (VL) chains of such antibodies. These fragments may have a molecular weight of approximately 13 kDa, or less than one-tenth the typical size of a full antibody.

Antigen-binding fragments of this type may be well expressed in bacterial, yeast, and mammalian cell systems. Such fragments may also be resistant to otherwise damaging conditions, such as freeze-drying or heat denaturation.

Antibodies of the invention may have both Variable and Constant domains. It will be appreciated that antigen-binding fragments (e.g. scFV antibodies) that comprise essentially the Variable region of an antibody without any Constant region are also encompassed by the present invention.

Antibodies of the invention may be "humanised" using techniques that will be well known to those skilled in the art. Humanisation may be at least partly achieved by engineering antibodies that use V region sequences from non-human (e.g. rodent) mAbs and C region (and ideally FRs from V region) sequences from human antibodies. The resulting 'engineered' mAbs are less immunogenic in humans than the rodent mAbs from which they were derived and so are better suited for clinical use, and are thus more susceptible to use in in vivo assays.

Further humanisation of antibodies may involve CDR-grafting or reshaping of antibodies. Such antibodies are produced by transplanting the heavy and light chain CDRs of a rodent mAb (which form the antibody's antigen binding site) into the corresponding framework regions of a human antibody.

It will be appreciated that, to at least some extent, the increased sensitivity of the monoclonal antibodies of the invention arises as a result of the specificity of their binding to AGR2. Accordingly it may be preferred that monoclonal antibodies of the invention bind specifically to AGR2, but not to similar or related proteins. It may be particularly preferred that a monoclonal antibody of the invention be one which does not bind to the protein anterior gradient 3 (AGR3). Indeed, so advantageous is this feature, that the invention also provides a monoclonal antibody having specificity for AGR2, while having no specificity for AGR3.

The antibodies of the invention are particularly well suited to use in diagnostic and/or prognostic applications. Accordingly, in a third aspect, the invention provides a method of diagnosing cancer, and particularly metastatic disease, using an antibody of the invention. In a fourth aspect, the invention provides a method of assessing a likelihood of developing cancer, and particularly metastatic disease, using an antibody of the invention. For the purposes of the present disclosure a "method of the invention" should be taken to encompass any diagnostic or prognostic use of the antibodies of the invention. Unless the context requires otherwise any method of the invention may be put into practice using any antibody of the invention.

Diagnostic use of the antibodies of the invention is particularly beneficial since the diagnostic sensitivity of assays using the antibodies of the invention is greatly increased over that which may be achieved using prior art techniques. Although they do not wish to be bound by any hypothesis, the inventors believe that this increased sensitivity of the diagnostic assays may derive from the increased sensitivity of the antibodies of the invention.

The inventors have found that the antibodies of the invention may be used in prognostic or diagnostic assays in which the ability of the antibodies of the invention to bind to tumour cells present in a patient's sample is assessed. The inventors have found that any binding of antibodies of the invention to tumour cells present in a patient sample may be considered as prognostically or diagnostically indicative of metastatic disease. In particular, binding of antibodies of the invention to approximately 1% or more of the tumour cells present in a patient sample is highly prognostic and/or diagnostic of metastatic disease.

Accordingly, an assay in accordance with the third or fourth aspects of the invention may comprise contacting a patient sample with a monoclonal antibody, or an antigen binding fragment thereof, according to the invention; and assaying for binding of the antibody to the patient sample, wherein binding of the antibody to the patient sample is diagnostic and/or prognostic of cancer, and particularly metastatic disease, in the patient. Preferably the patient sample may be a sample containing tumour cells. In this case, binding of the antibody of the invention (or antigen binding fragment thereof) to the tumour cells may be assessed. In the event that the antibody of the invention binds to tumour cells present in the patient sample, this is particularly diagnostic and/or prognostic of metastatic disease in the patient.

An assessment may be made as to the proportion of tumour cells in a patient sample that are bound by an antibody of the invention (or an antigen binding fragment thereof). For example, a prognostic and/or diagnostic result indicative of metastatic disease in the patient may be indicated by binding of the antibody (or antigen binding fragment thereof) to 1% or more of the tumour cells present in the patient sample.

Increased incidences of binding of the antibodies of the invention to tumour cells in a patient sample are associated with a reduction in the life expectancy of the patient from whom the sample is derived. In the event that an antibody of the invention binds to approximately 5% or more of tumour cells in a patient sample, this may indicated that the patient would benefit from rapid intervention to attempt to treat the cancer and possible metastases. Assays of this sort may also be used to determine suitable therapeutic regimes for the treatment of cancer, with those with relatively high binding of the antibodies of the invention (to approximately 5% or more of tumour cells present in a patient sample) representing suitable candidates for treatment with regimes that may be relatively harsh if such regimes would provide rapidly delivered benefits.

Diagnostic assays of the invention may be used beneficially to identify individuals suffering from cancer, and particularly metastatic disease. Diagnostic assays in accordance with the third aspect of the invention may comprise obtaining a patient sample, contacting the patient sample with an antibody of the invention, and assaying for binding of the antibody to the patient sample, wherein binding of the antibody to the patient sample is diagnostic of cancer, and in particular metastatic disease, in the patient. Binding of the antibody to the patient sample may be assayed by any relevant technique known to those skilled in the art, and a suitable technique may be selected by the skilled person with reference to the nature of any reporter moiety that may be attached to the labelled antibody. Suitable reporter moieties that may be used as labels attached to the antibodies of the invention are considered elsewhere in the specification.

It will be appreciated that the increased sensitivity of diagnostic assays disclosed herein has a number of advantages. The most important of these advantages is that diagnostic assays of the invention may allow the user a greater deal of confidence in the diagnostic result than in results provided by prior art assays. The increased sensitivity of the assays of the invention allows detection of AGR2 in patient samples at lower levels than has previously been the case. This allows earlier diagnosis of cancer, and particularly metastatic disease, than has been achievable using the prior art methods, and hence allows treatment to begin earlier after onset of the disease. Beginning treatment early is important in order to achieve maximum therapeutic effectiveness, and to thereby increase the chances of a patient's survival.

Diagnostic detection of AGR2 using the assays of the invention also allows the selection of appropriate therapeutic regimens for the treatment of cancer, and particularly metastatic disease, suffered by the patient. In particular, the inventors' findings suggest that patients in whom cancer (particularly metastatic disease) causes expression of AGR2 may be subject to significantly shorter survival than equivalent patients not expressing AGR2. This effect seems particularly noticeable in the case of estrogen-receptor$^+$ (ER$^+$) tamoxifen-treated patients. This finding indicates that expression of AGR2, which may be determined with greater certainty and sensitivity using the assays of the invention, is indicative of a form of metastatic disease that is apparently less severe, and characterised by ER$^+$ that do not respond well to hormone therapy. Accordingly, diagnosis using the assays of the invention may lead a clinician with responsibility for the diagnosed patient to avoid hormone therapy, and instead to choose alternative therapies likely to have greater beneficial results.

Finally, the increased sensitivity conferred by the assays of the invention means that a finding that no AGR2 is being expressed may be accepted with greater confidence as proof of the absence of metastatic disease. Thus patients receiving a diagnosis that metastatic disease is not present (or no longer present after successful therapeutic intervention) can have increased confidence that this finding is indeed correct.

In addition to the diagnostic uses set out above, the monoclonal antibodies of the invention are also susceptible to use in prognostic assays that may be used to assess a patient's risk of adverse clinical outcome due to development of cancer, and particularly metastatic cancer. A study by Innes et al. indicates that ER$^+$ patients exhibiting expression of AGR2 tend to suffer from reduced survival compared to similar patients in whom AGR2 is absent.

In particular the monoclonal antibodies of the invention may be used in prognostic assays that provide an indication as to how well a patient with cancer, and particularly metastatic cancer, will respond to treatment of the disease. Prognostic assays in accordance with the fourth aspect of the invention may comprise obtaining a patient sample, contacting the patient sample with an antibody of the invention, and assaying for binding of the antibody to the patient sample, wherein binding of the antibody to the patient sample indicates that the patient is unlikely to respond favourably to treatment of metastatic disease. Such patients may benefit from treatment using rigorous therapeutic regimes. Details of suitable rigorous treatment regimes that may be used to treat metastatic cancer may be determined with reference to the specific tissues or organs affected by the metastatic disease. Appropriate criteria for selection of suitable regimes will be apparent to one skilled in the art, and may, for example, be selected by a clinician responsible for the patient.

The inventors believe that assays of the invention may be used prognostically since detectable AGR2 expression may occur prior to development of clinically-detectable cancer, and particularly metastatic disease. Furthermore the inventors believe that expression of AGR2 by metastases might affect the behaviour or development of the metastases. Furthermore, AGR2 may be detectable in patient samples prior to development of clinically recognizable cancer, and particularly metastatic disease. Thus, the prognostic assays of the invention may allow identification of the presence of AGR2, and thus a patient has increased likelihood of a shorter survival as a result of the cancer or metastatic disease. Recognition of a patient's increased likelihood of reduced survival resulting from metastatic disease may allow prophylactic intervention (to prevent the further development of the disease) and/or increased monitoring for development of metastatic disease to allow treatment to be initiated early after the onset of disease.

Monoclonal antibodies in accordance with the present invention may be used in prognostic assays or diagnostic assays as described elsewhere in the specification. The inventors believe that assays using the monoclonal antibodies of the invention may in particular be used in diagnostic or prognostic assessment of cancers selected from the group consisting of: prostate cancer; ovarian cancer; and pancreatic cancer. It may be preferred that assessments of these selected cancers be conducted using assays of the invention, as described elsewhere in the specification.

The inventors have surprisingly found that monoclonal antibodies of the invention may also be used in the prognosis or diagnosis of diseases other than cancer. In particular, the inventors believe that monoclonal antibodies of the invention may be used for the prognostic or diagnostic assessment of inflammatory diseases. Rheumatoid arthritis represents a particularly preferred example of such an inflammatory disease that may be assessed prognostically or diagnostically using monoclonal antibodies in accordance with the present invention.

A prognostic or diagnostic assay for an inflammatory disease may comprise obtaining a patient sample; contacting the patient sample with a monoclonal antibody, or an antigen binding fragment thereof, which binds specifically to an epitope within the sequence KPGAKKDTKDSRPKL (Sequence ID No. 2); and assaying for binding of the antibody to the patient sample,
wherein binding of the antibody to the patient sample is prognostic or diagnostic for an inflammatory disease in the patient.

Any patient sample that may contain AGR2 protein may be used in the prognostic or diagnostic assays of the invention (whether in connection with cancer and metastatic disease or inflammatory diseases). These may include essentially acellular samples, such as urine, cerebrospinal fluid or lymph, into which AGR2 may be shed. Preferably a suitable sample may be a sample comprising cells capable of expression of AGR2. Examples of such samples include blood samples, or samples (such as biopsy samples) taken from other tissues. The inventors have found that histological samples or cryotomy samples may be of particular use in prognostic or diagnostic assays of the invention.

The antibodies and assays of the invention may be used prognostically or diagnostically in relation to many forms of cancer. Particular forms of cancer that may advantageously be investigated using the antibodies or assays of the invention include metastatic cancer; prostate cancer; ovarian cancer; and pancreatic cancer; breast cancer; stomach cancer; oesophageal cancer; and colon cancer. It will be appreciated that the diagnostic use of antibodies and assays of the invention may be particularly useful in the case of cancers that may otherwise be difficult to diagnose, including cancers at "interior" body sites (i.e. not palpable from the exterior of the body), such as pancreatic cancer or ovarian cancer; cancers that can otherwise remain "symptomless" for prolonged periods, such as stomach cancer; or cancers in which ARG2 appears to be highly expressed; such as colon cancers.

It will generally be preferred that the assays of the invention, whether prognostic or diagnostic, be used in connection with human patient samples.

Assays of the invention may utilise any suitable means for detecting binding of an antibody to its antigen that are known to those skilled in the art. Suitable methods may be selected with reference to the nature of any reporter moiety used to label the antibodies of the invention. Suitable techniques include, but are by no means limited to, flow cytometry (such as fluorescence activated flow cytometry—FACS) and enzyme linked immunosorbant assays (ELISAs), and assays utilising nanoparticles. It is particularly preferred that an assay of the invention be one involving immunocytochemistry in which tumour cells are exposed to an antibody of the invention, and the level of cell labelling assessed. Increased cell labelling will generally be indicative of poor clinical outcome. Suitable statistical analysis of the results of such assays may be conducted in accordance with the tests outlined in Example 2 of the Experimental Results section.

The invention also provides, in a fifth aspect, a hybridoma capable of producing an antibody, or an antigen binding fragment thereof, which binds specifically to an epitope within the sequence KPGAKKDTKDSRPKL (Sequence ID No. 2) of AGR2.

A "hybridoma of the invention" may be any hybridoma produced in accordance with the methods of the invention. Preferably a hybridoma of the invention will be a hybridoma capable of producing a monoclonal antibody of the invention. The hybridoma deposited as PZ7A10F10 under Accession Number 06082201 represents a particularly preferred example of a hybridoma of the invention.

A hybridoma producing the monoclonal antibody of the invention can be prepared by application of a routine immunization procedure using peptide fragment KPGAKKDTKDSRPKL (Sequence ID No. 2) of AGR2 as a sensitizing antigen, followed by a cell fusion procedure using a routine cell fusion technique, and a cloning procedure using a routine cloning technique.

In a suitable example, a non-human animal, such as a mouse, rat, rabbit, guinea pig, pig, sheep, goat or chicken may be the animal to be immunized. Preferably the animal to be immunised is a mouse or rat, and most preferably a mouse. The fact that myeloma cells used as the counterpart cell for a cell fusion are generally derived from mice, it may be particularly preferable to immunise mice when selecting the source of antibody-producing cells. The peptide fragment KPGAKKDTKDSRPKL (Sequence ID No. 2), corresponding to amino acid residues 26 to 40 of full length AGR2, is used as the sensitizing antigen. This antigen may be administered by any suitable route (for example, intraperitoneally, subcutaneously or to the footpad) to generate an immune response in the immunised animal. Preferably the immunising antigen may be administered by subcutaneous injection.

The skilled person will appreciate that antibodies of the invention may be generated using fragments of AGR2 comprising Sequence ID No. 2 (including full length AGR2) as an immunogen, followed by selection of hybridomas producing an antibody that binds to an epitope within KPGAKKDTKDSRPKL (Sequence ID No. 2).

Antibodies of the invention may be generated using AGR2 from species other than humans (or corresponding sequences of equivalent proteins from species other than humans) as long as antibodies having the required binding specificity are produced.

Immunisation to produce antibodies of the invention may be carried out using any suitable method known to the skilled person. For example, a suitable method may comprise administering a suitable dose of KPGAKKDTKDSRPKL (Sequence ID No. 2) diluted and suspended in a carrier such as phosphate-buffered saline, physiological saline or the like, to recipient animals on a weekly basis for one to three months.

Once a suitable regime of immunisation has been completed, spleen cells, lymphocytes, peripheral blood or other antibody-producing cells may be harvested from the immunised animals. Generally, cells from the spleen, excised after the last administration of the sensitising antigen may preferably be used as the antibody-producing cells. In any event, the harvested antibody-producing cells may then be subjected to cell fusion with particular strains of myeloma cells, a tumour cell line, to prepare hybridoma cells.

A range of suitable the myeloma cell lines that may be used in the production of hybridoma cells will be known to the skilled person. For example, cell lines, such as P3-NSI/1-Ag4-1 cells (briefly, NS-1 cells) (Kaehler et al., Eur. J. Immunol., 6:511 (1976)), SP2/0-Ag14 cells (briefly, SP2 cells) (Schulman et al., Nature, 276:269 (1978)), and FO cells (de-Saint Groth et al., J. Immunol. Meth., 35:1 (1980)) are all suitable for use to produce hybridomas in accordance with the present invention. It may be preferred to use SP2 cells. In order to facilitate recovery of the antibody of interest from a supernatant produced by hybridoma culture, it may be preferred to utilise a myeloma cell line that does not secrete the inherent immunoglobulin in myeloma cells. For example, it may be preferred to use NS-1 cells as myeloma cells for cell fusion.

Methods by which an antibody-producing cell and a myeloma cell can be fused are now a matter of routine procedure for those of skill in the art. Merely by way of example, cell fusion may be achieved in accordance with the protocol used by Kaehler and Milstein (Kaehler et al., 1975, Nature, 256; 495).

The cell fusion procedure may be carried out in an ordinary nutrient medium in the presence of a fusion promoter. Suitable fusion promoter that may be used to produce hybridomas in accordance with the present invention include, polyethylene glycol (PEG), or Sendai virus. Suitable PEG may have an average molecular weight of between 1,000 and 6,000. The cell fusion is carried out using antibody-producing cells and myeloma cells mixed in a predetermined ratio. Suitable ratios may range from about 1:1 to about 10:1. RPMI 1640 may be used as a culture medium in which cell fusion may take place, since this medium favours the growth of myeloma cells.

In order to effect cell fusion, the two kinds of cells (antibody-producing cells and myelomas) may be admixed in RPMI 1640 and maintained under normal cell culture conditions. A solution of polyethylene glycol may then be added in a concentration of 30 to 60% (w/v) to initiate cell fusion. Finally, once cell fusion has occurred, a further volume of a suitable medium may be added and the hybridoma produced recovered by centrifugation to remove the supernatant.

The recovered hybridoma may be selected by culture in an ordinary selection medium, such as HAT medium, which contains hypoxanthine (H), aminopterin (A) and thymidine (T). Culture in HAT medium may be continued for a period of between several days and a few weeks until cells other than the required hybridoma have been killed.

When the presence of colonies of the hybridoma is confirmed, the cultured supernatant may be screened for the presence of the monoclonal antibody. Suitable screening for the antibody in the culture supernatant may, for example, be carried out by assaying the antibody activity in the culture supernatant by an ELISA technique using immobilized cells as the antigen (Ando Tamie et al., Introduction to Monoclonal Antibody Experiment Protocols, K dansha Scientific (1993), pp. 126). It will be appreciated that suitable cells to be used in such a technique should be those that express AGR2, such as metastatic cancer cells. Once the presence of both the hybridoma and the desired monoclonal antibody has been confirmed the hybridoma may be cloned for further propagation using well-known techniques (for example ring cloning or cloning by limiting dilution).

Following the methods set out above allows the production, isolation and cloning of a hybridoma producing the monoclonal antibody of the invention. Suitable techniques for the maintenance of hybridomas are well known to those skilled in the art. For example, hybridomas can be cultured and subcultured using known cell culture media, such as RPMI 1640 or Dulbecco's modified essential medium (DMEM). Samples of hybridomas produced in the manner described above, and producing the monoclonal antibody of the invention, may be preserved in liquid nitrogen prior to thawing for future use.

Hybridomas of the invention are suitable for culturing on a large scale, to facilitate the production of large quantities of the antibodies of the invention. Hybridomas of the invention may, for instance, be cultured in 15% fetal calf serum (FCS)-RPMI 1640, and monoclonal antibodies of the invention can be prepared from the culture supernatant.

As an alternative, hybridomas of the invention may be injected intraperitoneally into experimental mice, to form ascite tumours. The monoclonal antibodies of the invention can then be prepared from the ascites fluid.

Monoclonal antibodies of the invention, however prepared, may be purified using well-known antibody purification techniques. Suitable examples of antibody purification technology that may be used to purify antibodies of the invention comprises precipitation (salting-out) with ammonium sulfate or the like, ion exchange chromatography using a diethylamino-ester (DEAE) derivative, a carboxymethyl (CM) derivative, or the like, hydroxyapatite chromatography, gel filtration chromatography, and affinity chromatography using Protein A or Protein G, among others, including binding to antigen against which the antibody has been raised. It will be appreciated that combinations of the techniques suggested above may be utilised in purification of the monoclonal antibody.

The invention also provides a method for the preparation of a monoclonal antibody of the invention, the method comprising immunising an animal with the peptide KPGAKKDTKD-SRPKL (Sequence ID No. 2), and then screening for and isolating the antibody.

The invention also provides a method for the preparation of a hybridoma producing an antibody of the invention, the method comprising immunizing an animal with the peptide KPGAKKDTKDSRPKL (Sequence ID No. 2), obtaining an antibody-producing cell from the immunized animal; and fusing the antibody-producing cell with a myeloma cell.

The skilled person will readily appreciate that the monoclonal antibodies of the invention may be used to generate antigen-binding antibody fragments. These may be generated by manipulation of the existing monoclonal antibodies, or using the monoclonal antibodies as a template for production of suitable fragments. Mechanisms by which such fragments may be produced will be well known to those skilled in the art.

Purely by way of example, Fab, F(ab')$_2$ and other immunoreactive fragments, can be obtained by digesting the monoclonal antibody of the invention with a proteolytic enzyme which does not decompose the antigen-binding site (Fab), such as papain, pepsin or the like. The antigen-binding fragments thus generated may then be isolated and purified using routine techniques. Antigen-binding fragments having the specificity of monoclonal antibodies of the invention can be used in the same way as the monoclonal antibodies themselves.

Monoclonal antibodies, or antigen-binding fragments, in accordance with the invention may be used in a number of assays (including, but not limited to, the diagnostic and prognostic assays of the invention), in which it may be beneficial to be able to obtain information as to the location or binding of the antibody or fragment. In such cases it may be preferred that the antibody, or antigen-binding fragment, be labelled using a reporter moiety. Such reporter moieties may be directly or indirectly linked to an antibody of the invention.

Suitable reporter moieties will be well known to those skilled in the art, as will methods by which they may be attached to the antibodies of the invention. A suitable reporter moiety may be selected from the group consisting of a fluorescent moiety; a luminescent moiety; a bioluminescent moiety; a radioactive material; a prosthetic group; a colorimetric moiety; a nanoparticles having suitable detectable properties, and a chromogenic moiety.

Purely by way of example, and without limitation, suitable fluorescent moieties may be selected from the group consisting of: fluorescein isothiocyanate (FITC); rhodamirie (TRITC); phycoerythrin; allophycocyanin; coumarin (AMCA); Texas red; and cyanine (Cy2, Cy3 or Cy5). Other suitable fluorescent moieties that may be used in labelling and antibodies of the invention will be readily apparent to the skilled person.

A suitable labelling of antibodies of the invention with FITC may be achieved using the following protocol. The antibody of the invention is prepared as a 2 mg/ml solution in 0.1M sodium carbonate (pH 9.0). FITC is dissolved in DMSO at 1 mg/ml and added slowly to the antibody solution (to a concentration of about 50 μg of FITC per ml of antibody). The mixture of antibody and FITC is incubated in dark for 8 hours at 4 degrees. After completion of this first incubation, NH4Cl is added to 50 mM, and the resultant mixture incubated for 2 hours at 4 degrees. Finally xylene cylanol and glycerol are added to 0.1% and 5% respectively. The labelled antibody of the invention may then be separated by gel filtration.

For the purposes of the present disclosure luminescent and bioluminescent moieties may be taken to encompass both moieties that have luminescent properties themselves, and moieties capable of giving rise to luminescent products. Luminol represents a suitable example of a luminescent moiety that may be used to label antibodies of the invention. Luciferase provides an example of a bioluminescent moiety (in this case a moiety able to generate a luminescent product) that may be used label antibodies of the invention.

Suitable radioactive materials that may be used to label antibodies of the invention will be apparent to the skilled person. Merely by way of illustrative example, suitable radioactive materials may include radioisotopes selected from the group consisting of: $^{125}$I; $^{131}$I; $^{35}$S; $^{3}$H; $^{14}$C; $^{32}$P; $^{99m}$Tc and $^{111}$In.

An antibody of the invention may be labelled using prosthetic groups that one another with high specificity. An example of such a suitable prosthetic group that will be well known to those skilled in the art is biotin. An antibody of the invention may be labelled with biotin, and the biotinylated antibody exposed to a specific binding partner for biotin (for example avidin or streptavidin). The binding partner may carry a separate label, such as a fluorescent label.

Colorimetric moieties that may be used to label antibodies of the invention include, but are not limited to: colloidal gold; and coloured glass or plastic (e.g. polystyrene, polypropylene, latex, or the like) beads.

Examples of chromogenic moieties that may be used to label antibodies of the invention include chromogenic enzymes such as: horseradish peroxidise and alkaline phosphatase. Various substrates that may be used to generate detectable products representative of activity of these enzymes are well known, and indeed are commercially available from many suppliers of laboratory reagents.

In addition to the direct labelling of antibodies of the invention, in which reporter moieties may be linked directly to the antibody or antigen-binding fragment, antibodies of the invention may also be labelled using indirect labelling techniques. Methods by which antibodies, such as the antibodies of the invention, may be indirectly labelled are well known to those of ordinary skill in the art.

One suitable manner by which antibodies of the invention may be indirectly labelled is by means of a "primary antibody"/"secondary" antibody strategy. Briefly, in such a strategy the unlabelled antibody of the invention is used as a "primary antibody" able to bind to AGR2 in a sample (e.g. a patient sample). A labelled "secondary antibody" (chosen to react solely with the antibody of the invention, and not with other materials in the sample) is then used to bind to the primary antibody. Thus the unlabelled antibody of the invention is effectively bound to the label attached to the secondary antibody.

The labelling of antibodies of the invention (whether directly or indirectly) allows detection of these antibodies. Typically unbound molecules carrying the chosen label (such as unbound directly labelled antibodies or secondary antibodies) will be removed from a sample so that substantially the only label remaining is associated with bound antibodies of the invention.

Detection of the label is then taken to represent detection of the bound antibodies of the invention. The means by which the label will be detected will depend on the nature of the label selected. For instance, a fluorescent label will be detected by illuminating the sample (containing the bound antibody of the invention) with light at the excitation wavelength of the fluorescent label, and detecting for the presence of light at the emission wavelength of the selected fluorophore.

An antibody labelled with a chromogenic enzyme may be detected by incubating the sample (containing the bound antibody of the invention) with a chromogenic substrate of the selected enzyme, and detecting for the presence of the coloured product produced as a result of action of the enzyme on the substrate.

Ways in which antibodies of the invention that have been labelled using alternative reporter moieties may be detected will be well known to those skilled in the art.

In further embodiments, the invention also provides kits for use in diagnostic or prognostic assays of the invention, the kits comprising a monoclonal antibody, or antigen-binding fragment thereof, of the invention. It will be appreciated that such kits may be used in the prognosis or diagnosis of one or more diseases selected from the group consisting of: cancer; (and particularly metastatic cancer; prostate cancer; ovarian cancer; pancreatic cancer; breast cancer; stomach cancer; oesophageal cancer; or colon cancer); an inflammatory disease generally; and rheumatoid arthritis in particular. Kits according to the present invention may also include additional components. Such components may, for example, include at least one item selected from the group consisting of: instructional materials (in any form, including printed or computer-readable materials); reagents for use in detecting antibody binding (including reagents, such as labelled secondary antibodies, that may be used in the visualisation of bound antibodies of the invention); reagents for use in antibody incubation (such as solutions that may be used for the dilution of primary or secondary antibodies, or reagents for use in chromogenic labelling protocols); and agents for the visualisation of cell nuclei. Preferred labelled secondary antibodies include fluorescently labelled antibodies, and antibodies labelled with a chromogenic agent. The antibody of the invention may be provided as one of a panel of reagents (such as suitable antibodies other than those of the invention) that have prognostic or diagnostic utility to be included in a kit in accordance with the invention.

The invention also provides a solid substrate to which is linked a monoclonal antibody, or antigen-binding fragment, of the invention. The substrate may, for example, comprise an array comprising antibodies of the invention. Suitable substrates may also include microbeads. It will be appreciated that the antibodies of the invention may be provided on a solid substrate as one of a panel of reagents (including antibodies other than those of the invention) that have prognostic or diagnostic utility.

The inventors believe that the antibodies of the invention may be able to block the function of AGR2 expressed by tumour cells. Given the exceptionally high specificity of the antibodies of the invention (as illustrated by their greater prognostic and diagnostic utility compared to previously disclosed antibodies) these antibodies may represent highly promising therapeutic agents, since they can target AGR2 without blocking the function of related components that are not involved in cancer progression. Accordingly, the invention provides an antibody, or an antigen binding fragment thereof, which binds specifically to an epitope within the sequence KPGAKKDTKDSRPKL (Sequence ID No. 2) of AGR2 for use as a medicament. The antibody, or antigen binding fragment, to be used in this aspect of the invention may preferably be a monoclonal antibody produced by the hybridoma PZ7A10F10.

Medicaments manufactured using the antibodies of the invention may be of use in the treatment of cancer, and in the prevention and/or treatment of metastatic disease (where the antibodies' ability to block AGR2 function may help to prevent the progression and dissemination of metastases). Suitable modifications of antibodies of the invention that are to be used as therapeutic agents will be apparent to those skilled in the art. Merely by way of example, it may be preferred to utilise fragments of such antibodies in the event that it is wished to achieve intracellular activity leading to a therapeutic effect. Additionally or alternatively, it may be wished to "humanise" the antibodies (as considered elsewhere in the specification) to reduce the likelihood of unwanted side effects caused by the patient's immune response to the exogenous antibody.

Antibodies of the invention, or antigen binding fragments of such antibodies, may also be used in the prevention and/or treatment of inflammatory diseases.

The amino acid sequence of AGR2 (Sequence ID No. 1) is illustrated in the Sequence Information section, along with the amino acid sequence of the sensitising antigen Sequence ID No. 2, a peptide fragment of AGR2. Amino acid residues 1-20 of Sequence ID No. 1 constitute a secretory signal sequence. The peptide fragment shown in Sequence ID No. 2 comprises amino acids 26-40 of Sequence ID No. 1.

The invention will now be further described with reference to the following Experimental Results and Figures in which:

FIG. 1 illustrates the results of western blotting to establish the specificity of the anti-AGR2 monoclonal antibody produced in accordance with Example 1. Lane 1 shown in FIG. 2 was loaded with 0.5 µg AGR2, whereas lane 2 was loaded with 0.5 µg AGR3. Antibody binding (detected via chemiluminescence) indicates that the monoclonal antibody bound strongly to AGR2 (shown by the strong signal in lane 1), but did not bind to AGR3 (indicated by the lack of signal in lane 3).

Figure 2:
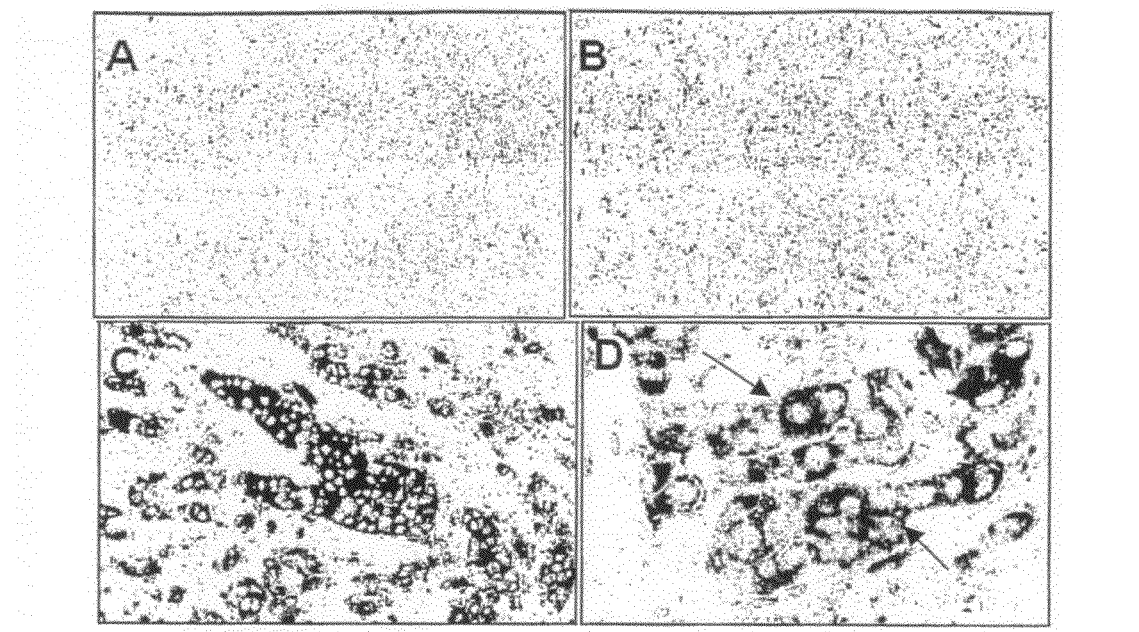

FIG. 2 shows immunocytochemistry of primary tumour patient samples using a monoclonal antibody of the invention to label AGR2. Panel 2A: normal breast; Panel 2B: a tumour section showing negative staining for AGR2; Panel 2C: a tumour section showing positive staining of the carcinoma cells; Panel 2D: a higher magnification of 2C showing strong immunocytochemical staining for AGR2. The arrows indicate the tumour cells that were positive stained for AGR2 using the antibody of the invention. Magnification A-C×40; D×125.

Figure 3:
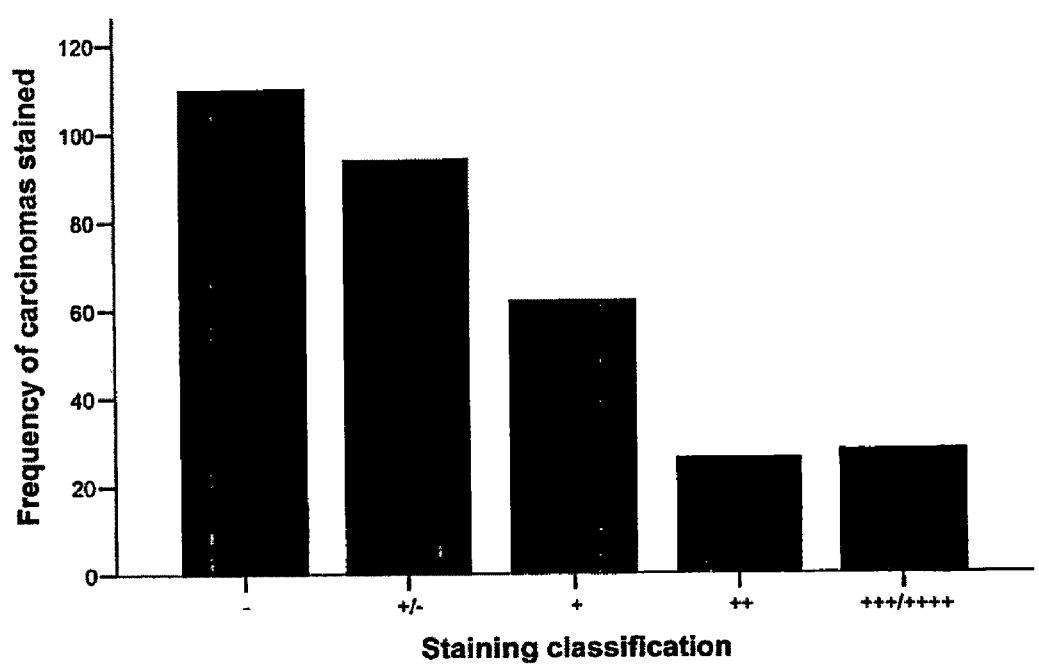

FIG. 3 shows frequency of the category of staining (in accordance with Table 1) of different carcinoma samples using an antibody in accordance with the invention. Primary carcinomas from 320 patients were immunocytochemically stained for AGR2 with monoclonal antibody of the invention.

Figure 4:
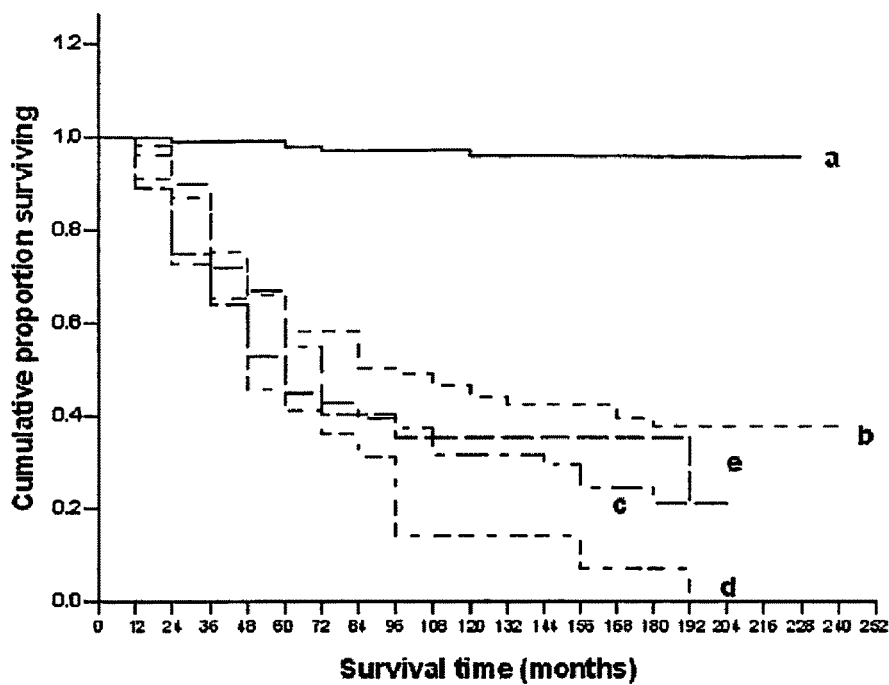

FIG. 4 shows survival plots for each staining category using the antibody of the invention. The cumulative proportion surviving represents the percentage of survival of patients in each staining category every 12 months over the study period of 240 months. 315 patients were assessed. (a, –) patients with negative staining for AGR2 (–), 100% for 107 patients; (b, -----) patients with borderline staining (+/–), 100% for 93 patients; (c, ---) patients with 5-25% staining (+), 100% for 61 patients; (d, ----) patients with 25-50% staining (++), 100% for 26 patients, and (e, --) patients with 50% or above staining (+++/++++), 100% for 28 patients. There were 103 censored observations in a (19 dead of other causes); 39 censored observations in b (16 dead of other causes); 17 censored observations in c (10 dead of other causes); 4 censored observations in d (4 dead of other causes) and 10 censored observations in e (9 dead of other causes). Overall the five plots are highly significantly different (Wilcoxon statistic $\chi^2$=103.157, 4 d.f., P<0.0001).

Figure 5:
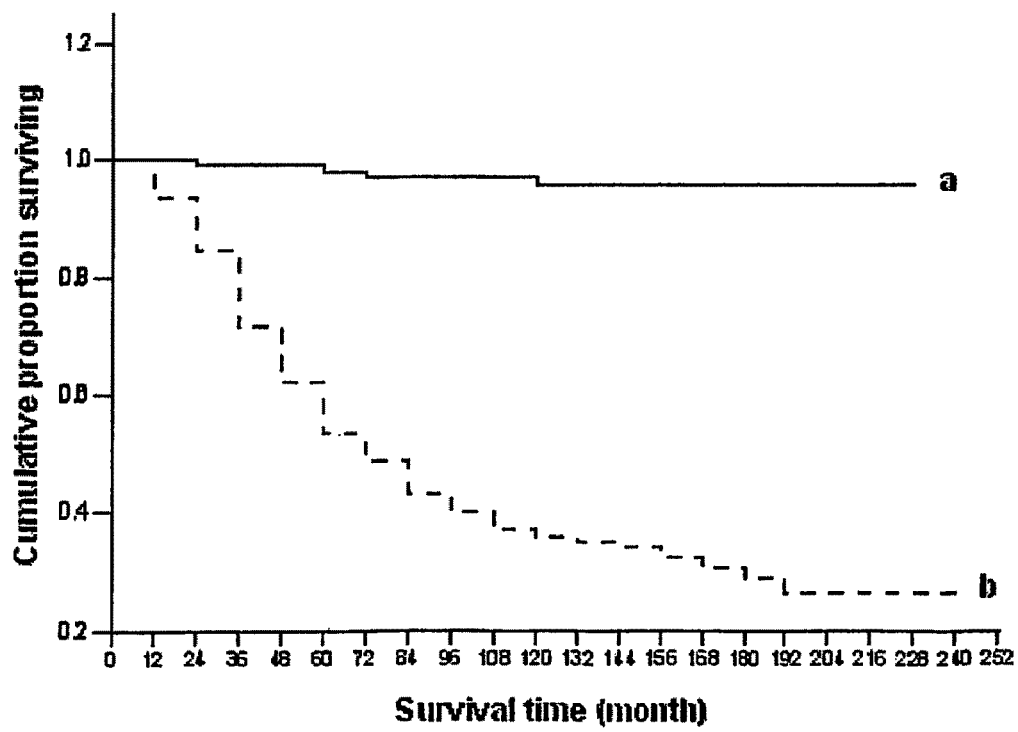

FIG. 5 shows survival plots for the negative (–), borderline (+/–) and all positive (+,++,+++/++++) staining groups for AGR2. The cumulative proportion of patient surviving represents the percentage of survival of patients in each staining category every 12 months over the study period of 240 months. 315 patients were assessed. (a, –), patients with negative staining for AGR2 (–), 100% for 107 patients; (b, ---), patients with borderline staining (+/–), 100% for 93 patients; (c, ----), patients with positive staining (+,++,+++/++++), 100% for 115 patients. There were 103 censored observations in a (19 dead of other causes); 39 censored observations in b (16 dead of other causes) and 31 censored observation in c (23 dead of other causes). The three plots were highly significantly different (Wilcoxon statistic $\chi^2$=101.49. 2 d.f., P<0.0001).

Figure 6:
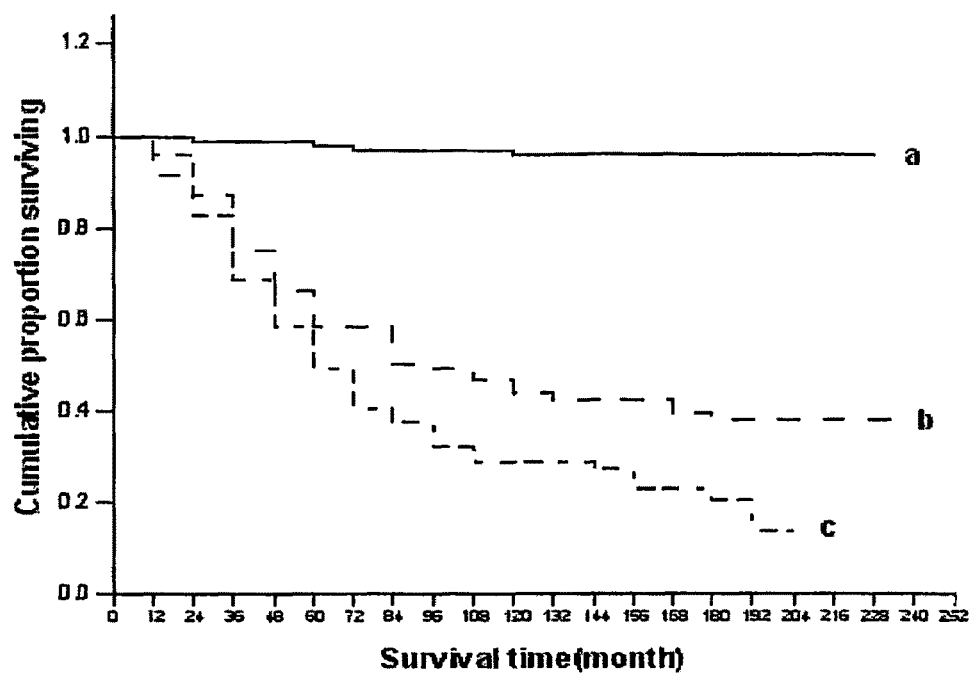

FIG. 6 shows survival plots for the negative (–) and for all other positive staining groups (+/–,+,++,+++/++++) using 1% cut-off level for AGR2 staining. The cumulative proportional of patients surviving represents the percentage of survival of patients in either staining category every 12 months over the study period of 240 months. 315 patients were assessed. (a, –), patients with negative staining for AGR2 (–). 100% for 107 patients. (b, -----), patients with borderline staining (+/–) grouped with all other positive staining groups (+,++,+++/++++). 100% for 208 patients. There were 103 censored observations in a (19 dead of other causes); and 70 censored observations in b (39 dead of other causes). The two plots were highly significantly different (Wilcoxon statistics $\chi^2$=97.40, 1 d.f, P<0.0001).

EXPERIMENTAL RESULTS

Example 1

Preparation of an AGR2 Specific Antibody-Producing Hybridoma, and Production and Isolation of AGR2 Antibody 1.1 Sensitizing Antigen The peptide fragment KPGAKKDTKDSRPKL (Sequence ID No. 2), representing amino acid residues 26 to 40 of AGR2 (as set out in Sequence ID No. 1) was synthesized de novo using standard synthetic procedures.

1.2 Immunisation

Four mice, aged between 6 and 8 weeks old were used as the host animals to be immunised. The peptide fragment KPGAKKDTKDSRPKL (Sequence ID No. 2) was used as the sensitising antigen. 50 µg/injection of the sensitising antigen KPGAKKDTKDSRPKL was administered by subcutaneous injection to the mice. Injections were administered on days 0, 21 and 42 (with a final boost before fusion) in order to stimulate an immune response against the antigen, and to trigger antibody production. Pre-immune serum was collected on day 0.

1.3 Preparation of a Hybridoma

Splenic lymphocytes of the best-responding mouse were fused with myeloma cells Sp2/O-Ag-14 using PEG (polyethylene glycol) and the resulting hybridomas seeded into 96 well plates for HAT selection. IgG-producing hybridomas were screened against the antigen. Positive colonies were expanded, tested for antibody production and reactivity against antigen (peptide) and against recombinant AGR2 protein. Selected hybridomas were cloned by limit dilution and screened against antigen (peptide) and against recombinant AGR2 protein. The selected hybridoma was used to isotype the antibody (G1; kappa) and for production and purification of the IgG.

1.4 Establishing Specificity of the Monoclonal Antibody

FIG. 1. Western blotting of the selected antibody on AGR2 and AGR3.

The ability of the monoclonal antibody to bind specifically to AGR2 was established by western blotting, as follows. Purified recombinant AGR2 (0.5 µg, Lane 1) and recombinant AGR3 (0.5 µg, Lane 2) proteins were subjected to polyacrylamide gel electrophoresis and blotted onto PVF membranes. These membranes were then blocked with a solution containing 5% non-fat milk and incubated with a 1 in 2,000 dilution of the anti-AGR2 monoclonal antibody overnight.

After overnight incubation, the membrane was washed and incubated for one hour with an HRP-conjugated anti mouse antibody. Bound antibody was detected by chemiluminescence with an ECL kit and exposure of the filter to photographic film.

The results of this experiment are shown in FIG. 1. In this Figure it can be sent that lane 1 shows a strong signal with the AGR2 protein (arrow), but no signal with the AGR3 protein. This result clearly indicates that the monoclonal antibody of the invention, produced in accordance with the protocol outlined above, is specific for AGR2.

Example 2

Diagnostic Use of the AGR2 Antibody

Immunocytochemical detection of AGR2 with a monoclonal antibody of the invention (produced as described in Example 1), in contrast to a conventional rabbit polyclonal antibody known from the prior art, enabled the discriminatory boundary between positive and negative staining tumours to be lowered from 5% to 1% of the carcinoma cells stained. Although they do not wish to be bound by any hypothesis, the inventors believe that this increased sensitivity arises as a result of the monoclonal antibody's lack of cross-reactivity with unrelated products e.g. AGR3.

The method of immunohistochemical staining of tissue sections with anti-AGR2/PZ7A10F10, the monoclonal antibody of the invention, is carried out as follows. Histological sections (cut at 4 μm) on APES coated (by a modification on the method of Maddox, P. H. and Jenkins, D.) slides were dewaxed in xylene and rehydrated through ethanol to water as previously described by Warburton et al. (1982). Microwave antigen retrieval was undertaken (Cuevas et al., 1994). Sections were immersed in 10 mM citrate buffer pH 6.0 and microwaved at 850 watts for 15 minutes using a domestic microwave oven. The slides were allowed to cool for a further 15 minutes while still immersed in the citrate buffer. Following antigen retrieval, endogenous peroxidase activity in the tissue sections was blocked by immersing the slides in 100% methanol containing 0.05% (v/v) $H_2O_2$ for 20 mins at room temperature (Streefkerk, 1972). Monoclonal antibody anti-AGR2/PZ7A10F10 was applied to the slides at a dilution of 1:100 in 0.5% BSA/PBS overnight at room temperature in a moisture chamber. Indirect immunocytochemical staining was carried out using a commercially available enhanced HRP labelled polymer system, the DAKO EnVision+System, peroxidase(DAB) (Dako Ltd, Ely, UK) (Heras, 1995), prepared according to the manufacturer's instructions. The sections were then washed in running tap water before being counterstained in Mayers' haemalum. They were then dehydrated through graded ethanol and xylene and were mounted in DPX mountant (Merck, Poole, UK).

Using these discriminatory levels (made available by the antibody of the invention and assays of the invention), the association of patient survival with time was significantly different between the positively-staining and negatively-staining tumours. The $\chi 2$ value of significance ($\chi 2$) (Wilcoxon statistics) and relative risk (RR) (Cox's univariate analysis) were $\chi 2=46.5$, RR=3.8 (95% CI 2.7-5.3) using the polyclonal antibody and $\chi 2=97.4$, RR=30.5 (95% CI 11-86) using the monoclonal.

This much higher association of positive immunocytochemical staining for AGR2 with early patient death obtained with the monoclonal antibody meant that when compared with other conventional markers (tumour size, histological grade, tumour-involved lymph nodes) and new markers (e.g. staining for S100A4, S100P, osteopontin, c-met, ERα, PgR, p53, cathepsin D, c-erbB-2), it became the most significant independent prognostic variable in a Cox's multivariate regression analysis test ($\chi 2=14.3$, P<0.001, RR=10; 95% CI 3-33).

Previously, the contribution to prognosis of conventional and new markers combined meant that staining for AGR2 using a polyclonal antibody was not independently associated with survival, its contribution being out-weighed by these other markers. Thus the monoclonal antibodies of the invention, and assays of the invention, provide notable advantages over the prior art.

Example 3

Diagnostic Use of the AGR2 Antibody—Second Study

In an expansion of the study reported above, breast cancer tissues from 320 patients who suffered from advanced breast cancer and were treated by mastectomy and radical mastectomy were investigated using the antibodies of the invention. This study sought to further investigate the prognostic and diagnostic utility of the antibodies of the invention.

The patients from whom the samples were derived presented between the years 1976 and 1982 to general surgery clinics in the Merseyside Region of the North West of England. This group of patients represented a fair reflection in the population as free medical treatment is available in the United Kingdom. The range of patients' ages was 29-92 with a mean age of 57 years. These patients were followed up for a mean period of 16 years with a range of 14-20 years. The patient survivals were updated to Aug. 31, 1995. The study further investigated the links between labelling of samples using the antibodies of the invention, and patient survival rates.

Immunolabeling using the monoclonal antibody anti-AGR2/7A10 (produced by the hybridoma PZ7A10F10) was undertaken using the protocols described for the preceding study (briefly immunolabeling of dewaxed histology sections, bound primary antibody being visualised by means of the Envision system in which production of a brown colour indicates antibody binding).

Analysis of Staining

Brown stains were seen when AGR2 was present. The percentage of cancerous cells stained was determined using light microscopy and this value used to allocate the sample to one of six groups, as shown in Table 1 below. Any minor immunolabeling of normal (non-tumour) cells was ignored for the purposes of the study.

Statistical Analysis

The survival analysis was carried out to determine any associations between the times of survival within each staining category in the full follow-up period of 240 months. Only those patients who died of cancer were analysed. The survival curves were constructed from life table using Kaplan-Meier plots and the survival data was analysed using the Wilcoxon (Gehan) Statistics. Patients who died of other causes other than cancer and who were dead at the end of the follow-up period were excluded from consideration. Cox's univariate regression analysis was undertaken to obtain the relative risk values with 95% confidence intervals for each of the categories being compared. Cox's multivariate regression analysis was also performed with all variables present to determine the relative significance between prognostic factors and to investigate whether patient survival with AGR2 was independent of these prognostic factors. A stepwise forward selection procedure was used. Cross Tabulation was used to compare patient groups separated into negative (unstained) and positive (stained) categories for two different prognostic markers. Two-tailed Fisher's Exact Test was performed to test for any significant difference between those tumours immunocytochemically stained for AGR2 and those positive for pathological markers or for chosen immunohistochemical markers (also believed to be of relevance in prognosis or diagnosis). The pathological markers used included histological grade, tumour size and nodal status while the immunocytochemical marker group included S100P, osteopontin, estrogen receptor α (ERα), c-erbB-2, c-erbB-3, S100A4, progesterone receptor (PgR), p53, cathepsin D, pS2 and c-met in the primary tumour. The data generated from AGR2 labelling using a monoclonal antibody of the invention, and the data generated in the previous study using polyclonal antibody as a comparison, were assessed for correlation using kappa function in Cross Tabulation. The kappa score was given to show whether there were possible agreements over chance between two variables. All statistical calculations were performed using the Statistical Package for the Social Sciences version 13.0 (SPSS Inc., Chicago, Ill., USA).

Results

Immunocytochemical Staining for AGR2 Using the Monoclonal Antibody

The majority of the normal breast was unstained by the monoclonal antibody to AGR2 (FIG. 2A) although there was very occasional faint staining of terminal ductal lobular units (FIG. 2B). This staining was readily distinguished from the staining observed in positively labelled cancer cells. The staining of carcinomas (FIG. 2C) was mainly located in the cytoplasm presenting a granular appearance and on the membrane (FIG. 2D).

Samples from the carcinomas were assessed for staining. Patients were divided into 6 categories according to the percentage of carcinoma cells bound by the antibody of the invention (in keeping with Table 1).

The ++++ group (above 75% carcinoma cells staining) was grouped with the +++ group (50-75% staining) due to the relatively small number of samples in these two categories. Of the 320 malignant samples evaluated, 110 (34%) did not contain cells that bound the antibody of the invention ("unstained" samples, shown as −), 94 (30%) exhibited binding of the antibody of the invention to less than 5% of the tumour cells present ("borderline staining", shown as +/−), 62 (19%) exhibited binding of the antibody to 5-25% of the tumour cells present (shown as +), 26 (8%) exhibited binding of the antibody of the invention to 25-50% of the tumour cells present (shown as ++) and 28 (9%) exhibited binding of the antibody of the invention to 50-100% of the tumour cells present (shown as +++). FIG. 3 shows the frequencies for each staining category.

Association of AGR2 with Other Pathological and Histological Variables

The immunocytochemical staining for AGR2 using monoclonal antibody was assessed using Cross Tabulation to compare it with other pathological and immunocytochemical variables. The pathological variables included histological grade, tumour size and nodal status while the immunocytochemical variables included staining for AGR2 using a polyclonal antibody, for S100P, osteopontin, estrogen receptor α (ERα), c-erbB-2, c-erbB-3, S100A4, progesterone receptor (PgR), p53, cathepsin D, pS2 and for c-met. The comparisons were made using two-by-two tables and were assessed using Fisher's Exact Test (2 tailed). The immunocytochemical staining for AGR2 was set at the 1% cut-level, i.e. the borderline group (+/−) was incorporated into the other positive staining groups, leaving the negative staining group as these tumours with less than 1% of stained carcinoma cells.

Table 2 shows the association of staining for AGR2 with other pathological variables. Only nodal status (P=0.036) showed a significant association with positive staining for AGR2. The comparison was also made at the 5% cut-off level for AGR2 staining (not shown), i.e. the borderline group (+/−) incorporated into the negative staining group (−), leaving the positive staining group consisting of all definitely positive carcinomas (+,++,+++/++++). Results were similar; however, the nodal status now showed only borderline (P=0.056) significance of association with the staining for AGR2.

Cross Tabulation of staining for AGR2 was undertaken initially at the 1% cut-off level. In contrast, staining for other tumour markers which showed an association with patient outcome in breast cancer was set at the level that achieved the most significant correlation, usually 5%. Of all the molecular variables, staining for S100P (P<0.0001), osteopontin (P<0.0001), ERα (P=0.002), c-erbB-3 (P=0.001), S100A4 (P<0.0001), PgR (P<0.0001), pS2 (P=0.004) and c-met (P<0.0001) showed a significant association with positive staining for AGR2.

If the cut-off level for staining for AGR2 was set at 5%, the significant of the results obtained was less than that at the 1% cut-off level (not shown). This indicates the surprisingly strong prognostic or diagnostic relevance of any binding of the antibody of the invention by tumour cells in a patient sample.

The Significance of AGR2 Staining Related to the Patient Survival

This second study was intended to investigate whether binding of an antibody of the invention to a patient sample (such as tumour cells in a primary tumour sample) is associated with length of patient survival in breast cancer. Reduced length of survival is generally associated with metastatic disease arising from primary tumours. In order to assess the association, survival curves for patients exhibiting different levels of antibody binding to tumour cells in their samples were plotted and compared (FIG. 4).

Using Wilcoxon Gehan statistics, there was an overall significant difference in survival times of patients with the 5 different categories of stained carcinomas (Wilcoxon test $\chi^2$=103.16, 4 d.f, P<0.0001). 96% of the 107 patients who were classified as negatively stained (−) were alive at the end of the study with a median survival time of >216 months. In the borderline staining group (+/−), the cumulative proportion of patient surviving was 38% for 93 patients and the median survival time was 87 months. For those patients with tumours that showed 5-25% (+) of positive staining using the antibody of the invention, the cumulative proportion surviving was 21% and the median survival time was 65 months. There were no survivors (0%) amongst the 26 patients in the group with tumours containing 25-50% (++) of carcinoma cells binding the antibody of the invention, and the median survival time was only 45 months. For those patients whose tumours contained greater than 50% of carcinoma cells (+++/++++) that bind an antibody of the invention, the cumulative proportion surviving for 28 patients was 21% and the median survival time was 52 months (FIG. 4). The relative risk (R.R.) and its 95% confidence interval (95% C.I.) corresponding to different combinations of staining category are detailed in Table 4.

In FIG. 6, of the 107 patients whose tumour cells were classified as not binding an antibody of the invention, 96% of them survived until the end of the study with a median survival time of >216 months. The cumulative proportion surviving for those who showed positive staining for AGR2 (+/−,+,++,+++/++++) was 26% at the end of the study with a median survival time of 69 months. The R.R. was high at 30.5 with 95% CI., 11.3-82.5 (FIG. 6). This illustrates that any binding of an antibody of the invention to tumour cells present in a patient sample is prognostic and/or diagnostic for metastatic disease. That this is a more accurate and sensitive marker than binding using other anti-AGR2 antibodies known from the prior art is clearly indicated by the results of the preceding study (in which the diagnostic/prognostic utility of antibodies in accordance with the invention was compared with that of known polyclonal antibodies raised against AGR2).

Determining Whether Patient Survival with AGR2 was Independent of Other Prognostic Factors Survival data for samples containing tumour cells that bind to antibodies of the invention, and comparable data from all pathological and most tumour variables that were assessed previously using Cross Tabulation were entered into a Cox's multiple regression analysis (Materials and Methods). Staining for AGR2 was set at the optimum 1% cut-off level while staining for most of the other parameters was set at the optimum 5% cut-off levels for patient survival in univariate analysis. Staining for c-erbB-3 and pS2 were omitted from the analysis, since they did not show significant correlation in univariate analysis with patient survival in this particular group of patients. Cathepsin D was set at 1% cut-off level as only this cut-off showed significance in univariate analysis in a previous study with this particular group of patients. Of all factors investigated, only binding of an antibody of the invention, or staining using osteopontin, c-erbB-2, ERα c-met and S100A4 were independent and reached significantly associated with patient survival times. The presence of cells that bind an antibody of the invention (shown as "AGR2") was found to be the most significant independent variable with respect to patient survival in this analysis (Table 5).

Sequence Information

Sequence ID No. 1 (Amino acid sequence of human AGR2)

```
mekipvsafl llvalsytla rdttvkpgak kdtkdsrpkl
pqtlsrgwgd qliwtqtyee alyksktsnk plmiihhlde
cphsqalkkv faenkeiqkl aeqfvllnlv yettdkhlsp
dgqyvprimf vdpsltvrad itgrysnrly ayepadtall
ldnmkkalkl lktel
```

Sequence ID No. 2 (Amino acid sequence of sensitising antigen)

```
       kpgakkdtkdsrpkl
```

Tables

| Percentage of tumour cells stained (%) | Classification |
|---|---|
| <1 | − |
| 1-5 | +/− |
| 5-25 | + |
| 25-50 | ++ |
| 50-75 | +++ |
| 75-100 | ++++ |

Legend to Table 1.
Classification of patients with breast cancer based on immunolabelling in the primary tumour using antibodies of the invention. System used based on the percentage of malignant cells that labelled positively using an antibody of the invention.

TABLE 2

Association of staining for AGR2 at the 1% cut-off level with pathological variables.

| Pathological variables (no. of patients) | AGR2[a] (−) Number (%) | AGR2[a] (+) Number (%) | Fisher's Exact Test[b] (2 tail) |
|---|---|---|---|
| Grade (total 285) | | | |
| Grade 1, 2 | 67 (75.3) | 146 (74.5) | 1.000 |
| Grade 3 | 22 (24.7) | 50 (25.5) | |
| Tumour (total 304) | | | |
| T1, 2 | 83 (80.6) | 150 (74.6) | 0.256 |
| T3, 4 | 20 (19.4) | 51 (25.4) | |

TABLE 2-continued

Association of staining for AGR2 at the 1% cut-off level with pathological variables.

| Pathological variables (no. of patients) | AGR2[a] (−) Number (%) | AGR2[a] (+) Number (%) | Fisher's Exact Test[b] (2 tail) |
|---|---|---|---|
| Nodes (total 231) | | | |
| Node (−) | 48 (63.2) | 75 (48.4) | 0.036 |
| Node (+) | 28 (36.8) | 80 (51.6) | |

Legend to Table 2
[a]Immunocytochemical staining for AGR2 at the 1% cut-off level. (−) indicates the negative group while (+) indicates all other positive groups including the borderline staining group (+/−).
[b]Fisher's Exact Test (2-tailed) was used to assess the significance of any association between AGR2 and other pathological variables. Those that were significant (P < 0.05) are shown in bold print.

TABLE 3

Association of staining for AGR2 at the 1% cut-off level with staining for molecular markers.

| Staining for molecular[a] variables (no. of patients) | AGR2[b] (−) Number (%) | AGR2[b] (+) Number (%) | Fisher's Exact Test[c] (2 tail) |
|---|---|---|---|
| S100P (total 280) | | | |
| S100P (−) | 82 (82.0) | 51 (28.3) | <0.0001 |
| S100P (+) | 18 (18.0) | 129 (71.7) | |
| Osteopontin (total 306) | | | |
| OPN (−) | 74 (68.5) | 29 (14.6) | <0.0001 |
| OPN (+) | 34 (31.5) | 169 (85.4) | |
| ERα (total 313) | | | |
| ERα (−) | 64 (58.7) | 81 (39.7) | 0.002 |
| ERα (+) | 45 (41.3) | 123 (60.3) | |
| C-erbB-2 (total 314) | | | |
| c-erbB-2 (−) | 87 (80.6) | 155 (75.2) | 0.324 |
| c-erbB-2 (+) | 21 (19.4) | 51 (24.8) | |
| C-erbB-3 (total 309) | | | |
| c-erbB-3 (−) | 58 (53.7) | 67 (33.3) | 0.001 |
| c-erbB-3 (+) | 50 (46.3) | 134 (66.7) | |
| S100A4 (total 318) | | | |
| S100A4 (−) | 96 (87.3) | 96 (46.2) | <0.0001 |
| S100A4 (+) | 14 (12.7) | 112 (53.8) | |
| PgR (total 305) | | | |
| PgR (−) | 79 (75.2) | 109 (54.5) | <0.0001 |
| PgR (+) | 26 (24.8) | 91 (45.5) | |
| p53 (total 318) | | | |
| P53 (−) | 71 (65.1) | 122 (58.4) | 0.277 |
| P53 (+) | 38 (34.9) | 87 (41.6) | |
| CathepsinD (total 249) | | | |
| Cath D (−) | 38 (47.5) | 66 (39.1) | 0.218 |
| Cath D (+) | 42 (52.5) | 103 (60.9) | |
| pS2 (total 315) | | | |
| pS2 (−) | 76 (69.7) | 108 (52.4) | 0.004 |
| pS2 (+) | 33 (30.3) | 98 (47.6) | |
| C-met (total 280) | | | |
| c-met (−) | 56 (57.7) | 28 (15.3) | <0.0001 |
| c-met (+) | 41 (42.3) | 155 (84.7) | |

Legend to Table 3
[a]Immunocytochemical staining for molecular variables at 5% cut-off level. − and +/− are grouped as (−) and +, ++, +++/++++ are grouped as (+).
[b]Immunocytochemical staining for AGR2 at the 1% cut-off level. (−) indicates the negative group and (+) indicates all other groups (+/−, +, ++, +++/++++).
[c]Fisher's Exact Test (2-tailed) was used to assess any significant association between staining for AGR2 and staining for other molecular variables. Those that were significant (P < 0.005) are shown in bold print.

TABLE 4

Pairwise comparison between each staining category for AGR2.

| staining categories[a] | $\chi^{2b}$ | d.f.[c] | P[d] | R.R.[e] | 95% C.I.[e] |
|---|---|---|---|---|---|
| Overall | 103.16 | 4 | <0.0001 | N.A. | N.A. |
| − and +/− | 68.19 | 1 | <0.0001 | 24.1 | 8.71-66.6 |
| − and + | 84.27 | 1 | <0.0001 | 33.9 | 12.1-94.8 |
| − and ++ | 84.80 | 1 | <0.0001 | 52.9 | 18.1-155 |
| − and +++ | 60.18 | 1 | <0.0001 | 36.1 | 12.2-107 |
| +/− and + | 1.08 | 1 | 0.298 | 1.41 | 0.94-2.10 |
| +/− and ++ | 4.53 | 1 | 0.033 | 2.20 | 1.33-3.63 |
| +/− and +++ | 1.71 | 1 | 0.192 | 1.50 | 0.88-2.56 |
| + and ++ | 2.36 | 1 | 0.124 | 1.56 | 0.93-2.61 |
| + and +++ | 0.656 | 1 | 0.418 | 1.07 | 0.62-1.84 |
| ++ and +++ | 0.026 | 1 | 0.871 | 1.46 | 0.78-2.73 |

Legend to Table 4
[a] Staining categories for AGR2 are defined in Table 1 and pairwise comparisons correspond to those in the survival plots of FIG. 5.
[b] $\chi^2$ test using Wilcoxon statistics.
[c] Degrees of freedom.
[d] Probability values from $\chi^2$. Those P values which were significance are shown in bold print.
[e] Relative risk for patient survival (R.R.) and 95% confidence interval (95% C.I.) from Cox's multiple regression analysis.

TABLE 5

Results of Cox's multiple regression analysis using all pathological and most molecular variables.

| Tumour variables[a] | β[b] | SE[c] | $\chi^{2d}$ | d.f. | P[e] | R.R.[f] | 95% C.I.[f] |
|---|---|---|---|---|---|---|---|
| mAGR2 | 2.30 | 0.61 | 14.3 | 1 | <0.0001 | 10.0 | 3.03-33.1 |
| Osteopontin | 1.65 | 0.61 | 7.31 | 1 | 0.007 | 5.23 | 1.58-17.3 |
| c-erbB-2 | 0.82 | 0.31 | 6.83 | 1 | 0.009 | 2.27 | 1.23-4.21 |
| ERα | −0.65 | 0.27 | 5.59 | 1 | 0.018 | 0.52 | 0.31-0.90 |
| c-met | 1.61 | 0.76 | 4.52 | 1 | 0.034 | 5.00 | 1.13-22.0 |
| S100A4 | 0.54 | 0.31 | 2.97 | 1 | 0.085 | 1.71 | 0.93-3.16 |

Legend to Table 5
[a] Tumour variables which showed a significant and independent association with patient survival in multivariate analysis. Those variables that did not reach an independent significant level with patient survival were S100P, histological grade, tumour size, nodal status, p53, PgR, Cathepsin D.
[b] Value of β parameter in the Cox's multiple regression analysis.
[c] Standard error of β.
[d] $\chi^2$ Statistics generated from Cox's multiple regression analysis.
[e] Probability from $\chi^2$. Overall $\chi^2$ = 77.83, 7d.f., P < 0.0001.
[f] Relative risk (R.R) for patient survival and 95% confident interval (95% C.I.) from multivariate analysis.

REFERENCES

Innes H. E., Liu D., Barraclough R., Davies M. P. A., O'Neill P. A., Platt-Higgins A., de Silva Rudland S., Sibson D. R. and Rudland P. S. (2006). Significance of the metastasis-inducing protein AGR2 for outcome in hormonally-treated breast cancer patients. Br. J. Cancer 94, 1057-1065

Maddox, P. H. and Jenkins, D., 3-Aminopropyltriethoxysilane (APES): a new advance in section adhesion. J Clin Pathol. 1987; 40:1256-1257

Warburton, M. J., Mitchell, D., Ormerod, E. J., and Rudland, P. S. Distribution of myoepithelial cells and basement membrane proteins in the resting, pregnant, lactating and involuting rat mammary gland. (1982) J. Histochem. Cytochem., 30: 667-676

Cuevas, E. C., Bateman, A. C., Wilkins B. S. et al. Microwave antigen retrieval in immunocytochemistry: a study of 80 antibodies, (1994) J. Clin. Pathol., 47, 448-452

Streefkerk, J.G. Inhibition of erythrocyte pseudoperoxidase activity by treatment with hydrogen peroxide following methanol. (1972) J. Histochem. Cytochem., 20, 829

Hems, A. et al. Enhanced labelled-polymer system for immunohistochemistry. XVth Eur Cong Pathol. Copenhagen, Denmark 1995; September 3-8

The invention claimed is:

1. A monoclonal antibody, or an antigen binding fragment thereof, which binds specifically to an epitope within the sequence KPGAKKDTKDSRPKL (SEQ ID No.:2) of AGR2, and wherein the monoclonal antibody or antigen binding fragment thereof does not bind to AGR3.

2. The monoclonal antibody, or antigen-binding fragment thereof, of claim 1, that binds to the same epitope as does the monoclonal antibody produced by the hybridoma PZ7A10F10.

3. The monoclonal antibody, or antigen binding fragment thereof, of claim 1, wherein the antibody or fragment is labelled with a reporter moiety selected from the group consisting of a fluorescent moiety; a luminescent moiety; a bioluminescent moiety; a radioactive material; a prosthetic group; a colorimetric moiety; a detectible nanoparticles; and a chromogenic moiety.

4. The monoclonal antibody, or antigen-binding fragment thereof, of claim 3, wherein the antibody or fragment is labelled with a fluorescent moiety selected from the group consisting of: fluorescein isothiocyanate (FITC); rhodamine (TRITC); phycoerythrin; allophycocyanin; coumarin (AMCA); Texas red; and cyanine (Cy2, Cy3 or Cy5).

5. The monoclonal antibody, or antigen-binding fragment thereof, of claim 1, produced by the hybridoma PZ7A10F10.

6. A method of diagnosing cancer using an antibody, or an antigen binding fragment thereof, which binds specifically to an epitope within the sequence KPGAKKDTKDSRPKL (SEQ ID No.:2), and wherein the antibody or antigen binding fragment thereof does not bind to AGR3.

7. The method of claim 6, comprising: obtaining a patient sample; contacting the patient sample with a monoclonal antibody, or an antigen binding fragment thereof, which binds specifically to an epitope within the sequence KPGAKKDTKDSRPKL (SEQ ID No.:2), and wherein the monoclonal antibody or antigen binding fragment thereof does not bind to AGR3; and assaying for binding of the antibody to the patient sample,
wherein binding of the antibody to the patient sample is diagnostic of metastatic disease in the patient.

8. A method of assessing a likelihood of developing cancer, comprising: obtaining a patient sample; contacting the patient sample with a monoclonal antibody, or an antigen-binding fragment thereof, which binds specifically to an epitope within the sequence KPGAKKDTKDSRPKL (SEQ ID No.: 2); and assaying for binding of the antibody to the patient sample,
wherein binding of the antibody to the patient sample indicates that the patient has an elevated likelihood of developing metastatic disease.

9. The method of claim 6, wherein the cancer is a metastatic cancer.

10. The method of claim 7, wherein assaying for binding of the antibody to the patient sample utilizes immunocytochemistry labelling of a tissue sample.

11. The method of claim 7, wherein the assaying for binding of the antibody to the patient sample utilizes an enzyme linked immunosorbent assay (ELISA).

12. The method of claim 7, wherein the assaying for binding of the antibody to the patient sample utilizes fluorescence activated cell sorting (FACS).

13. The method of claim 7, wherein the patient sample comprises tumor cells, and the assay comprises assaying for binding of the antibody, or antigen binding fragment thereof, to tumor cells in the patient sample.

14. The method of claim 7, wherein the patient sample is selected from the group consisting of: a blood sample; a biopsy sample; a histology sample; and a cryotomy sample.

15. A kit comprising a monoclonal antibody, or an antigen-binding fragment thereof, which binds specifically to an epitope within the sequence KPGAKKDTKDSRPKL (SEQ ID No.:2), and wherein the monoclonal antibody or antigen binding fragment thereof does not bind to AGR3.

16. The kit of claim 15 comprising a monoclonal antibody, or antigen-binding fragment thereof, produced by the hybridoma PZ7A10F10.

17. The kit of claim 15, further comprising at least one item selected from the group consisting of: instructional materials for using the kit; reagents for use in detecting antibody binding; reagents for use in antibody incubation; and agents for the visualization of cell nuclei.

18. A hybridoma PZ7A10F10.

* * * * *

SEQUENCE LISTING

<160> NUMBER OF SEQ ID NOS: 2

<210> SEQ ID NO 1
<211> LENGTH: 175
<212> TYPE: PRT
<213> ORGANISM: Homo sapiens

<400> SEQUENCE: 1

```
Met Glu Lys Ile Pro Val Ser Ala Phe Leu Leu Leu Val Ala Leu Ser
1               5                   10                  15

Tyr Thr Leu Ala Arg Asp Thr Thr Val Lys Pro Gly Ala Lys Lys Asp
            20                  25                  30

Thr Lys Asp Ser Arg Pro Lys Leu Pro Gln Thr Leu Ser Arg Gly Trp
        35                  40                  45

Gly Asp Gln Leu Ile Trp Thr Gln Thr Tyr Glu Glu Ala Leu Tyr Lys
    50                  55                  60

Ser Lys Thr Ser Asn Lys Pro Leu Met Ile Ile His His Leu Asp Glu
65                  70                  75                  80

Cys Pro His Ser Gln Ala Leu Lys Lys Val Phe Ala Glu Asn Lys Glu
                85                  90                  95
```

```
Ile Gln Lys Leu Ala Glu Gln Phe Val Leu Leu Asn Leu Val Tyr Glu
            100                 105                 110

Thr Thr Asp Lys His Leu Ser Pro Asp Gly Gln Tyr Val Pro Arg Ile
            115                 120                 125

Met Phe Val Asp Pro Ser Leu Thr Val Arg Ala Asp Ile Thr Gly Arg
            130                 135                 140

Tyr Ser Asn Arg Leu Tyr Ala Tyr Glu Pro Ala Asp Thr Ala Leu Leu
145                 150                 155                 160

Leu Asp Asn Met Lys Lys Ala Leu Lys Leu Leu Lys Thr Glu Leu
                165                 170                 175

<210> SEQ ID NO 2
<211> LENGTH: 15
<212> TYPE: PRT
<213> ORGANISM: Homo sapiens

<400> SEQUENCE: 2

Lys Pro Gly Ala Lys Lys Asp Thr Lys Asp Ser Arg Pro Lys Leu
1               5                   10                  15
```